USO08897857B2

(12) United States Patent
Tomé et al.

(10) Patent No.: US 8,897,857 B2
(45) Date of Patent: Nov. 25, 2014

(54) METHOD AND APPARATUS FOR GENERATING PROTON THERAPY TREATMENT PLANNING IMAGES

(75) Inventors: Wolfgang Axel Tomé, Madison, WI (US); Dongxu Wang, Madison, WI (US); Thomas R. Mackie, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 143 days.

(21) Appl. No.: 13/285,875

(22) Filed: Oct. 31, 2011

(65) Prior Publication Data
US 2013/0108014 A1 May 2, 2013

(51) Int. Cl.
*A61N 5/10* (2006.01)
*A61B 5/00* (2006.01)
*A61B 6/00* (2006.01)
*A61B 6/03* (2006.01)

(52) U.S. Cl.
CPC ............. *A61B 6/5217* (2013.01); *A61B 6/032* (2013.01); *A61B 6/50* (2013.01); *A61B 6/505* (2013.01); *A61B 5/4869* (2013.01); *A61N 2005/1087* (2013.01); *A61N 2005/1061* (2013.01); *A61B 6/544* (2013.01); *A61N 5/103* (2013.01)
USPC ............... 600/427; 378/21; 378/65

(58) Field of Classification Search
USPC ....................... 600/427; 378/21, 65
See application file for complete search history.

(56) References Cited

U.S. PATENT DOCUMENTS 6,245,005 B1 * 6/2001 von Gutfeld et al. ............. 600/1

OTHER PUBLICATIONS

Schaffner et al., "The precision of proton range calculations in proton radiotherapy treatment planning: experimental verification of the relation between CT-HU an dproton stopping power". Phys. Med. Biol. 43. 1998. pp. 1579-1592.*
Langen et al., "Initial Experience with Megavoltage (MV) CT Guidancefor Daily Prostate Alignments". Int. J. Radiation Oncology Biol. Phys. vol. 62, No. 5, 2005. pp. 1517-1524.*
Schulte et al., "Proton Computed Tomography for Clinical Applications". Loma Linda University. 2002.*
Schneider et al., "Patient specific optimization of the relation between Ct-Hounsfield units and proton stopping power with proton radiography". Medical Physics. vol. 32, No. 1. 2005. pp. 195-199.*

* cited by examiner

*Primary Examiner* — Long V. Le
*Assistant Examiner* — Colin T Sakamoto
(74) *Attorney, Agent, or Firm* — Boyle Fredrickson, S.C.

(57) ABSTRACT

A method of producing a patient image indicating proton stopping power of the tissue may employ photon attenuation information converted to proton stopping power. The conversion uses different conversion functions for particular tissue types to account for a strong atomic number dependency in the conversion process. Megavoltage x-rays may be used for improved accuracy.

19 Claims, 3 Drawing Sheets

METHOD AND APPARATUS FOR GENERATING PROTON THERAPY TREATMENT PLANNING IMAGES

STATEMENT REGARDING FEDERALLY SPONSORED RESEARCH OR DEVELOPMENT

Not Available

CROSS REFERENCE TO RELATED APPLICATION

Not Available

BACKGROUND OF THE INVENTION

The present invention relates to treatment planning for radiation therapy of tumors and the like and in particular for treatment planning system providing an improved assessment of the proton stopping power of tissue being treated.

External-beam radiation therapy may treat a tumor within a patient by directing high-energy radiation in one or more beams toward the tumor. Selective disruption of tumor tissue is obtained both by concentrating radiation at the site of the tumor and by taking advantage of a greater susceptibility of tumor tissue to radiation, for example, resulting from its higher cell division rate.

Photon external-beam radiation systems, for example, as manufactured by Accuray, Inc., of Sunnyvale Calif., treat a tumor with multiple x-ray fan beams directed at the patient over an angular range of 360°. Each of the beams is comprised of individually modulated "beamlets" whose intensities can be controlled so that the combined effect of the beamlets, over the range of angles, allows complex treatment areas and dose patterns to be defined.

X-ray photons deposit energy in tissue along the entire path between the entrance and the exit point in the patient, necessarily irradiating healthy tissue along the path to the tumor. This drawback has suggested the use of heavy charged particles, such as protons alpha particles or carbon ions, as a substitute for x-ray photon radiation. Unlike x-rays, protons or heavier ions may be controlled to stop within the tissue, reducing or eliminating exit dose through healthy tissue on the far side of the tumor. Further, the dose deposited by a proton beam is not uniform along the entrance path of the beam, but rises substantially to a "Bragg peak" near a point where the proton beam stops within the tissue. By positioning the Bragg peak inside the tumor, the entrance dose through healthy tissue may be substantially reduced with respect to the dose deposited in the tumor.

The accuracy possible with proton beam therapy is best exploited if a treatment plan is prepared tightly defining the dose to the patient with respect to a precise characterization of the patient tissue such as may be obtained from an image of the patient tissue, for example a set of CT slices covering the tumor area. A treatment plan tied to such images may permit a physician to accurately demarcate within the images a region to be treated and a dose within that region. The identified region may then be used to calculate the orientation, energy and intensity of multiple proton beams that will produce the demarcated dose and treatment area.

Converting a description of the treatment area and dose to orientation, energy, and intensity of multiple proton beams requires an understanding of the proton stopping power of the tissue along the path of the protons. This knowledge allows adjustment of the energy of the proton beam to position the Bragg peak precisely within the tumor site.

A conventional x-ray CT image can provide information about the attenuation of x-ray photons but is a relatively poor proxy for proton stopping power leading to errors of 3 to 5 percent in practice employing the best known conversion methods. It is known that generating tomographic images using the proton beam itself instead of x-ray photons is a more accurate way of obtaining proton stopping power information. Protons entering and exiting the patient are detected by position and direction detectors (for example silicon strip detectors), and then collected by an energy detector (for example a scintillation detector) for residual energy detection. Such detected proton data form a proton sinogram that describes the summation of proton stopping powers for different proton beamlets across the patient at a range of beam angles. The proton sinogram is further used to reconstruct a tomographic image that contains the proton stopping power values of each spatial location of the body tissues within the patient. This tomographic image is used for proton therapy treatment planning.

A drawback to this approach arises from the limited energy of therapeutic proton beams of approximately 200-250 MeV. This proton energy is insufficient for the protons to traverse more than approximately 25 to 38 centimeters of tissue before entering the Bragg peak region at which point the either deposit significant energy or stop in the tissue, and therefore, for many patients, the image sinogram provided by the proton beam will be incomplete, leading to severe image artifacts that obscure the quantitative data that must be extracted for treatment planning.

Methods of reconstructing tomographic images when the underlying sinogram is incomplete are known in the x-ray CT art, however, the large and continuous regions of missing data likely in a proton sinogram, and the need for quantitative accuracy in the proton sinogram, make these x-ray CT techniques generally inapplicable.

SUMMARY OF THE INVENTION

The present inventors have recognized that the inaccuracy attendant to converting x-ray photon attenuation to proton stopping power using a conventional x-ray CT image can be greatly reduced by segmenting the tissues into different tissue types on the conventional x-ray CT image, then converting each segment from x-ray attenuation to proton stopping power using different conversion functions. The derived proton stopping power for each segment can be used to reconstruct an entire a proton stopping power image or blended with an available proton sinogram having data obtained through actual measurement with a proton beam.

Specifically then, the invention may provide a program and/or an electronic computer receiving data of a patient based on photon attenuation of x-ray photons passing through patient tissue and identify at least two tissue types of the tissue. At least a portion of the photon attenuation data is converted to derived proton stopping-power data using different conversion functions Unique to each tissue type and the derived proton stopping power data is used to produce a treatment control sequence defining proton energies along different paths through the patient tissue according to a treatment plan.

It is thus a feature of at least one embodiment of the invention to overcome tissue thickness limitations on proton imaging by enabling accurate conversion of x-ray attenuation data to proton stopping power in projection space. It is another feature of at least one embodiment of the invention to provide accurate proton stopping power data using readily obtainable photon imaging.

The photon attenuation data may provide attenuation of megavoltage photons.

It is thus a feature of at least one embodiment of the invention to further improve the accuracy of the conversion process by using a photon energy range showing less tissue type variation.

Alternatively, the photon attenuation data may provide attenuation of kilovoltage photons.

It is thus a feature of at least one embodiment of the invention to provide proton stopping power data using conventional x-ray CT machines operating in the kilovolt range.

The program and/or electronic computer may receive partial proton stopping power data of the patient insufficient to reconstruct a tomographic image, and the production of the treatment control sequence may use the derived proton projection data to complete the partial proton projection data to reconstruct a tomographic image revealing proton stopping power.

It is thus a feature of at least one embodiment of the invention to blend the converted proton projection data with actual proton projection data for improved accuracy.

Alternatively, the derived proton projection data may be sufficient to reconstruct a tomographic image, and the tomographic image revealing proton stopping power may be used to produce the treatment control sequence.

It is thus a feature of at least one embodiment of the invention to provide a system eliminating the need for proton imaging.

The program and/or electronic computer may calibrate the conversion functions by analyzing the attenuation of x-ray photons along different paths through the patient through different tissue types. This calibration may mathematically combine attenuation of x-ray photons through different combinations of the different tissue types to isolate an attenuation value for each tissue type.

It is thus a feature of at least one embodiment of the invention to provide a method of calibrating the conversion functions to the particular patient for improved accuracy.

These particular objects and advantages may apply to only some embodiments falling within the claims and thus do not define the scope of the invention.

DETAILED DESCRIPTION OF THE PREFERRED EMBODIMENT

Figure 1:
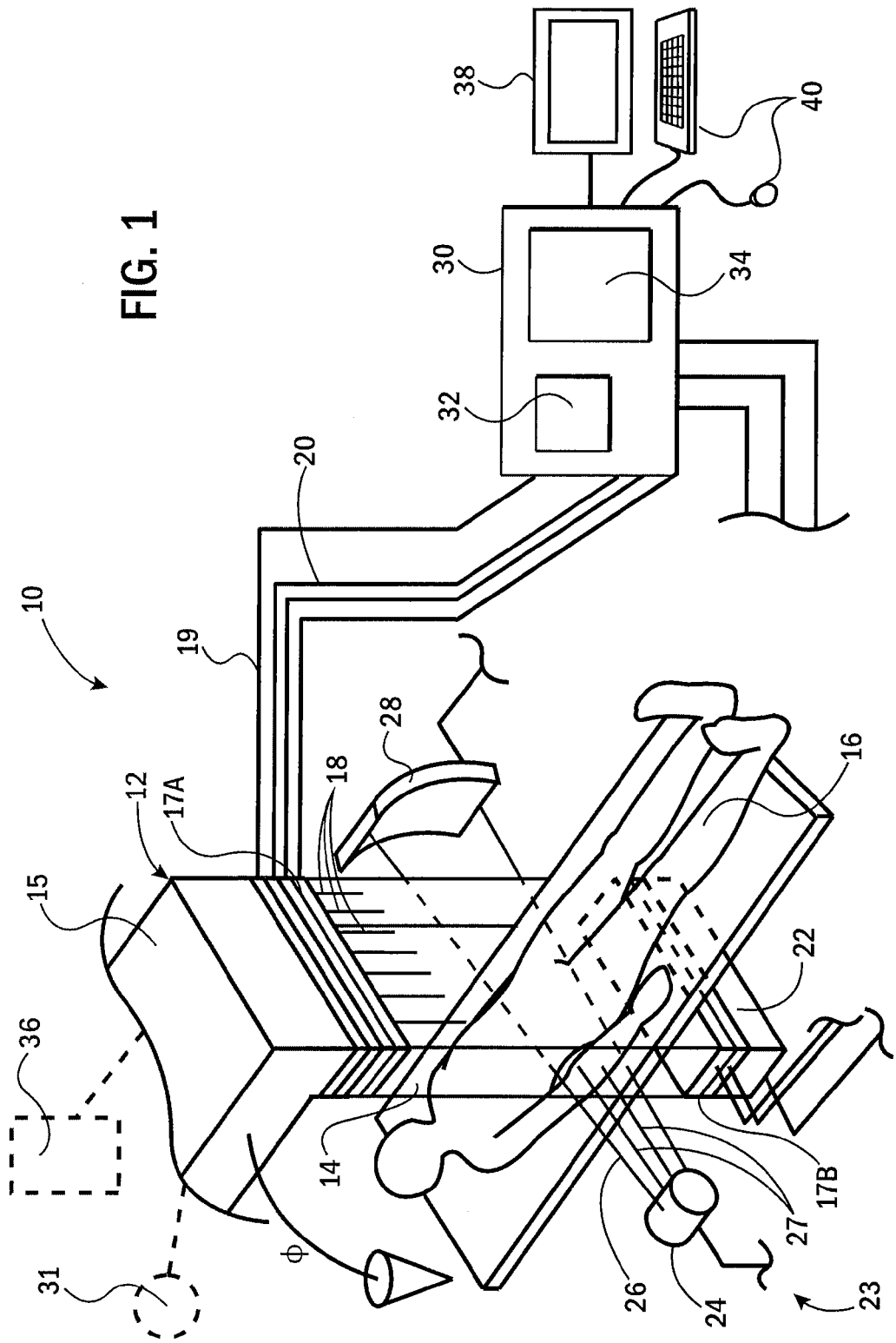
FIG. 1 is a simplified perspective view of a proton treatment system with an integrated x-ray CT machine communicating with an electronic computer for executing a treatment planning program suitable for use with the present invention.

Referring now to FIG. 1, a combined proton therapy and imaging system 10 suitable for use of the present invention may provide a proton source 12, for example, being a repositionable accelerator (such as, but not limited to a dielectric wall accelerator) or an exit port of a conduit conducting a proton beam from a stationary cyclotron, for example using a series of quadrupole or other suitable magnetic directors.

The proton source 12 may be rotatable on a gantry 15 to direct a proton beam 14 at a patient 16 at a range of gantry angles $\phi$ about the patient 16, driven by a gantry drive 36. The proton beam 14 may be an areal beam or a scanned pencil beam and may be controlled in energy at a variety of different locations within the beam 14 according to an energy signal 19 controlling an accelerating voltage of the accelerator or material places in the beam such as a range shifter used to provide a pencil beam or the placement of an energy reducing filter into an areal beam 14. An intensity signal 20 may likewise control the proton fluence of each of the beamlets 18 either by controlling an accelerator source current or placing fluence reducing filters into an areal beam 14.

For imaging purpose, before actual proton therapy is performed, proton beam 14 passes through a set of position and direction detectors 17a and 17b (such as a silicon strip detectors) positioned in the proton beam before and after the patient 16 and may be measured by a portal monitor 22 to collect projection data analogous to x-ray projection data used for CT scanning and indicating residual energy of the protons in each of the beamlets 18.

The combined proton therapy and imaging system 10 may also include an x-ray CT system 23 comprising an x-ray photon source 24 (e.g. an x-ray tube) positioned to project x-rays 26 through the patient 16 to be received by x-ray detector 28 distinguishing the attenuation of the x-rays along multiple x-ray beamlets 27 through the patient 16.

An electronic computer 30 may receive signals from the position and direction detectors 17a and 17b, the portal imaging device 22, the x-ray detector 28, and an angle sensor 31 providing the value of the gantry angle $\phi$ and may provide control signals to control the x-ray source 24 and gantry drive 36 (controlling the gantry angle $\phi$) and may provide the energy signal 19 controlling the energy of the individual beamlets 18 and the fluence signal 20 controlling the fluence of the individual beamlets 18.

Generally, the electronic computer 30 may include a processor 32 executing a stored program 34 to operate in one of three modes. A first mode produces essentially constant energy and fluence in the beamlets 18 and records output (proton projections) from the position and direction detectors 17a and 17b and the portal monitoring device 22 for each gantry angle $\phi$ and each beamlet 18 to generate at least a part of a proton sinogram, such as may be used to reconstruct a tomographic image indicating proton stopping power. A second mode operates the x-ray CT device to collect cumulative x-ray attenuation (x-ray projections) over a range of gantry angles $\phi$ for multiple beamlets 27 of the x-ray beam 26 to generate an x-ray sinogram, such as may be used to reconstruct a tomographic image indicating x-ray attenuation. The third mode outputs a treatment control sequence controlling the irradiation of the patient with protons from the proton beam 14 at various gantry angles $\phi$. The treatment control sequence defines the energy and intensity of each of the beamlets 18 as a function of angle $\phi$ using energy signal 19 and fluence signal 20.

The electronic computer 30 may also provide output to a graphic display monitor 38 (such as an LCD or CRT screen) for the display of text and graphics may receive input from user input devices 40 (such as a cursor control device and keyboard).

Figure 2:
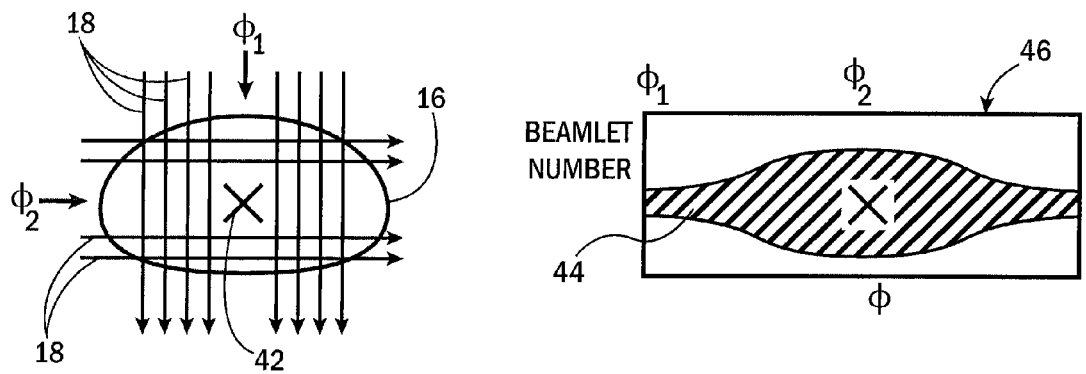
FIG. 2 is a cross-sectional view of a patient in the proton treatment system of FIG. 1 and undergoing proton imaging, and a corresponding sinogram having missing data caused by limited range of the protons.

Referring now to FIG. 2, when the machine 10 is operating in the first mode to collect a proton sinogram, and is positioned at a first angle $\phi_1$ in which the protons pass through the patient in an anterior to posterior direction, protons may be wholly blocked by a region 42 presenting greater than approximately 40 centimeters of tissue along the axis of propagation of the protons. Such blockage will cause a missing data 44 in the proton sinogram 46 for center beamlets 18 passing through region 42. Likewise at a perpendicular gantry angle $\phi_2$, in which the protons may pass through the substantially greater width of tissue presented from a left to right side of the patient, the region 42 may block a substantially larger number of the center beamlets of the sinogram 46 expanding the size of the missing data 44. In general there may be more than one such blocking region 42 of different sizes depending on the patient dimensions. In most cases, the missing sinogram data 44 can be substantial and continuous throughout the range of projection angles $\phi$ making it difficult to reconstruct a proton tomographic image having quantitative accuracy.

Figure 3:
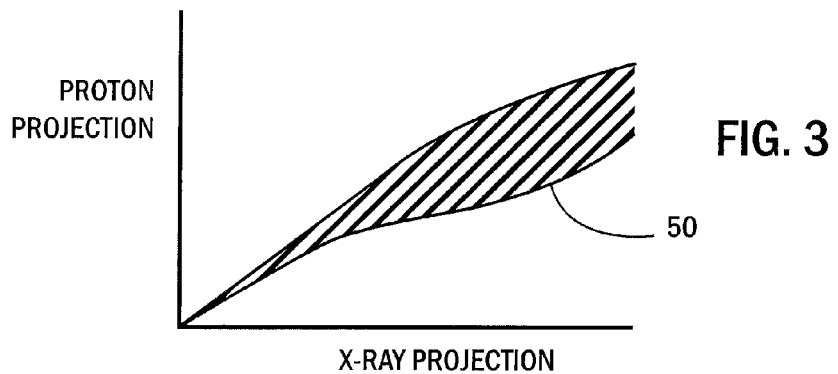
FIG. 3 is a graph showing proton stopping power versus x-ray photon attenuation for a cross-section through the human body indicating an inherent inaccuracy in the functional relationship that limits the ability to convert photon attenuation to proton stopping power.

Referring now to FIG. 3, an empirical measure of a relationship between proton projections indicating cumulative proton stopping power along a given beamlet 18 and x-ray projection indicating cumulative x-ray attenuation along a corresponding beamlet 27 aligned with beamlet 18, for example using megavoltage measurements of a realistic phantom, show a substantial functional imprecision represented by a spreading of a graph line 50 relating these two quantities. Generally the imprecision is greater at the kilovoltage level. For this reason, any attempt to convert x-ray photon projections, for example, taken with the x-ray CT machine of FIG. 1 directly into proton stopping power along corresponding rays (proton projections), will yield substantial errors.

Figure 4:
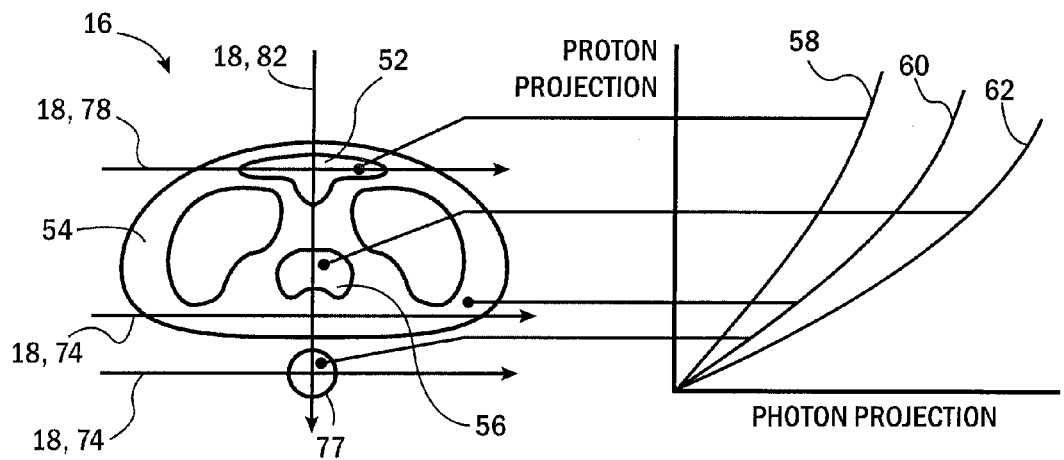
FIG. 4 is a depiction of a photon tomography image of the patient segmented into different tissue types, each tissue type linked to a graph similar to that of FIG. 3 showing improved conversion accuracy.

Referring now to FIG. 4, the present inventors have determined that if the tissue of the patient 16 is segregated into different tissue types and the relationship between corresponding proton projections and x-ray photon projections is analyzed in isolation for each tissue types, a much more accurate functional relationship between photon projection and proton projection may be derived. In one embodiment, the present invention considers at least three different tissue types including: adipose tissue 52 (being generally body fat), non-adipose tissue 54 being generally watery tissue, and bone tissue 56. The relationship between photon projection and proton projection for each of these tissue types may be plotted in a graph similar to that of FIG. 3 to produce distinct curves including adipose curve 58 (being a function $p_A=\Pi_a(\xi)$) and associated with adipose tissue 52, non-adipose curve 60 (i.e. a function $p_B=\Pi_b(\xi)$) associated with non-adipose tissue 54, and bone curve 62 (being a function $p_C=\Pi_c(\xi)$) associated with bone tissue 56. In each of these functions, p is the proton projection as a function of the x-ray projection $\xi$ through the same particle path in that tissue type.

As an initial matter, the particular functions of curves 58, 60 and 62 may be determined empirically (for example, using realistic phantom materials) and stored as simplified polynomial representations in the computer 30 (shown in FIG. 1). For x-ray CT that uses megavoltage energy, there exists theoretical relationship between the curves 58, 60 and 62, which may facilitate the determination of these three curves as will be described below.

Generally, the present invention uses the curves 58, 60, and 62 for each of these tissue types separately to provide a highly accurate conversion between photon projection and proton projection.

Figure 5:
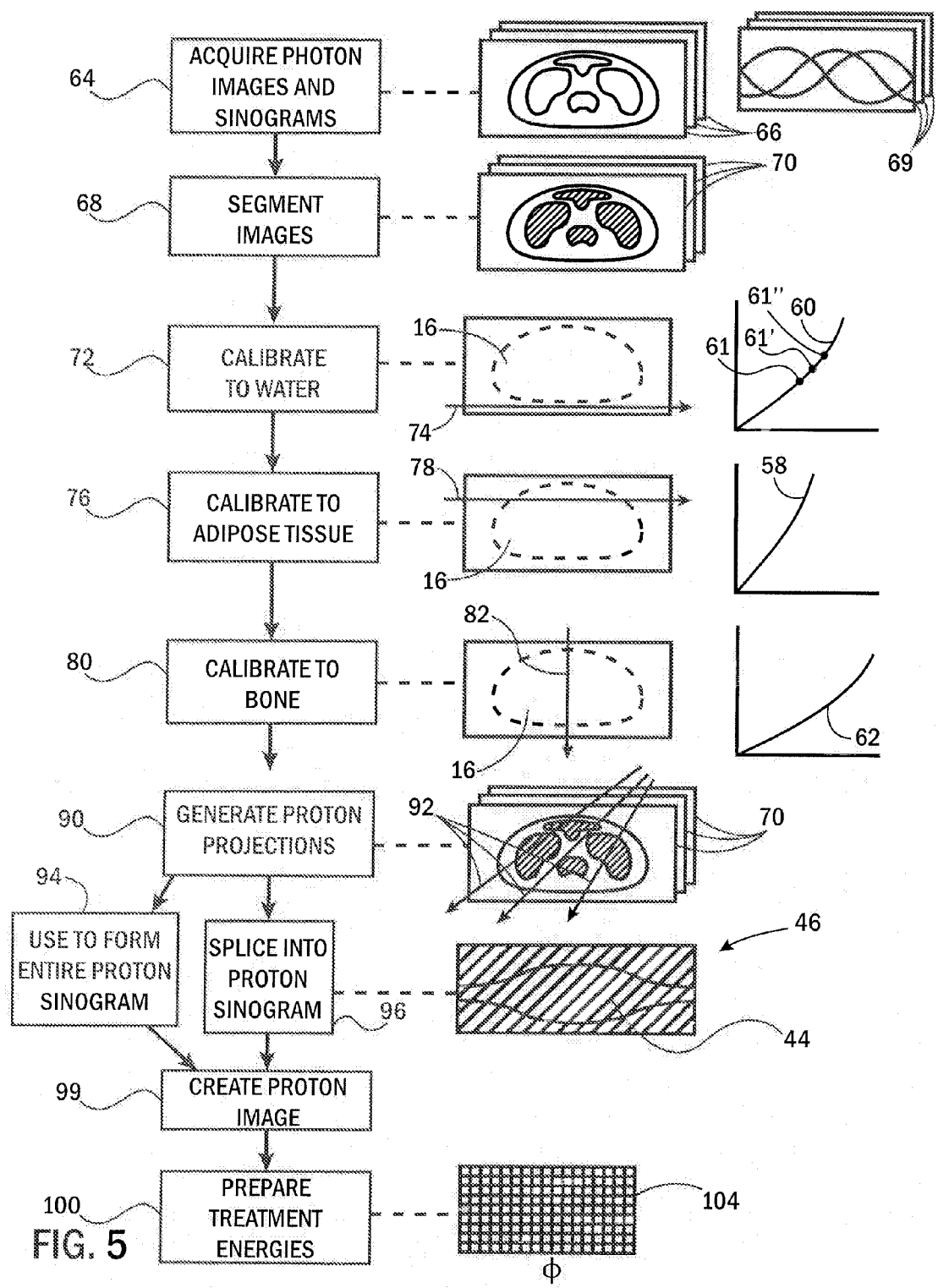
FIG. 5 is a flowchart of a program executable on the computer FIG. 1 together with data diagrams showing principal steps of the present invention.

Referring now to FIG. 5, the present invention may be implemented using the program 34 on a computer 30 to first acquire a set of photon tomographic images 66 along with their corresponding photon sinograms 69 as indicated by process block 64. These images may be acquired on the system 10 or on a separate x-ray computer tomography system with the patient 16 transferred to the system 10 and registered appropriately. These photon tomographic images 66 may be obtained with either megavoltage or kilovoltage x-rays and provide a set of pixels, each representing a Hounsfield Unit value as is understood in the art.

At process block 68, the set of photon tomographic images 66 may be segmented into the different tissue types described above and each of those tissue types demarcated for example by surrounding them in an outline providing segmented images 70. The segmentation process may be performed manually by a physician but more typically will be automatic or semiautomatic relying on known anatomical templates and ranges of Hounsfield Units to auto segmented tissue appropriately.

At process block 72, the machine 10 may be adjusted to direct a proton beam 14 along an axis 74 to intercept with at least one beamlet 18 passing through only non-adipose tissue or in this case, its equivalent in the form of a water phantom 77 positioned near the patient 16. This irradiation provides a proton projection value $p_B$ associated with a given photon projection $\xi_B$ (as determined from the sinogram in block 64, the segmentation of process block 68, and knowledge of the axis 74, or measured separately in the case of using a water phantom 77), and forms a data point 61. By changing the length of the beamlet 18 traversing through non-adipose tissue or water phantom 77, data points 61' and 61" similar to 61 can be found. A curve connecting these data points with a polynomial fit can be produced as the calibration curve 60 particular to non-adipose tissue or water.

Next, at process block 76, the machine 10 may be adjusted to direct the proton beam 14 along an axis 78 so that at least one beamlet 18 passes through a combination of non-adipose tissue 54 and adipose tissue 52 only. This provides proton projection data value $p_A+p_B$ for given photon projection $\xi_{A+B}$ (determined from photon sinogram) through the same combination of adipose tissue 52 and non-adipose tissue 54, and forms one data point for the combined adipose tissue and non-adipose tissue. By generating many of these points and using the calibration curve 60 particular to non-adipose tissue, and knowledge about the respective amounts of each type of tissue from the segmentation of process block 68, the proton projection values $p_A$ at different $\xi_A$ for adipose tissue may be separated out through algebraic processes such as those solving for simultaneous equations or a least square fit, producing calibrating curve 58 that is particular to adipose tissue.

At process block 80, machine 10 may be adjusted to direct a proton beam along an axis 82 through all three tissue types of adipose tissue 52, non-adipose tissue 54, and bone tissue 56. This provides proton projection data values $p_A+p_B+p_C$ for corresponding photon projection $\xi_{A+B+C}$ (determined from the photon sinogram) through the same combination of non-adipose tissue 54, the adipose tissue 52 and the bone tissue 56, and forms one data point for the combined adipose tissue, non-adipose tissue, and bone. By generating many of these points and using knowledge about the respective amounts of each type of tissue along each ray path from the segmentation of process block 68, the calibrated curves 60 and 58, the proton projection values $p_C$ at different $\xi_C$ for bone may be separated out through a least square fit, producing calibrating curve 62 that is particular to bone.

For example, the adipose curve 58 may be determined from the combined readings of adipose tissue and non-adipose tissues as follows:

$$\Pi_a(\xi_i) = p_i \frac{HU_A(\xi_i) + HU_B(\xi_i)}{HU_A(\xi_i)} - \frac{HU_B(\xi_i)}{HU_A(\xi_i)} \Pi_b(\xi_i)$$

Specifically, in the case of using megavoltage x-ray for generating photon tomographic images and photon sinogram, there exists constant ratios between $p_A$, $p_B$ and $p_C$ when $\xi_A = \xi_b = \xi_C$. Once curve 60 is known, curve 58 and 62 can be found by simply multiplying the constant ratios to curve 60, simplifying the calibration procedure. The constant ratios may be derived theoretically based on the average atomic numbers of the different tissue types or determined through experiment.

Referring to process block 90, the segmented image may then be re-projected mathematically by defining multiple ray lines 92 through the segmented image 70 as if a physical patient were being imaged using protons. For a ray line 92, the photon projection value $\xi$ is already known from the photon sinogram; through this ray line the amount of particular tissue type A, B, or C can be found from the segmentation and expressed in Hounsfield Units (HU) as $HU_A(\xi)$, $HU_B(\xi)$, and $HU_C(\xi)$ The proton projection value p along the same ray line is converted from the photon projection $\xi$ by averaging the individual conversion of these different tissue type and amount according to the following equation:

$$p = \frac{HU_A(\xi) \cdot \Pi_a(\xi) + HU_B(\xi) \cdot \Pi_b(\xi) + HU_C(\xi) \cdot \Pi_c(\xi)}{HU_A(\xi) + HU_B(\xi) + HU_C(\xi)}$$

Referring still to FIG. 5, rays 92 may be generated for all beamlets 18 for each gantry angle $\phi$ to produce a proton sinogram as indicated by process block 94, or selected derived proton projections 92 may be identified to fill in the missing data 44 of the proton sinogram 46 as indicated by process block 96.

As indicated by process block 100, the proton sinogram 46 obtained through either process block 94 or 96 may then be used to reconstruct a proton stopping power image at process block 99, which is further used in a treatment planning process to determine necessary energies of each proton beamlet 18 for the desired gantry angles $\phi$ to create a treatment control sequence 104 for controlling the machine 10. Generally the treatment control sequence 104 need not include every beamlet 18 or all gantry angles $\phi$ as is understood in the art.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

Use of the term "image" means any data associated with spatial locations corresponding to an image that may be obtained of the patient.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A proton therapy treatment program stored in a non-transitory computer-readable storage medium executable on an electronic computer to perform the steps of:
   (a) receiving photon attenuation data of a patient based on attenuation of x-ray photons passing through patient tissue;
   (b) segmenting the received photon attenuation data into at least two tissue types;
   (c) receiving a first proton projection value for a proton beamlet passing through a first of the at least two tissue types of the patient tissue while avoiding a second of the at least two tissue types, and receiving a second proton projection value for a proton beamlet passing through the first and the second of the at least two tissue types;
   (d) converting at least a portion of the photon attenuation data to derived proton stopping-power data using first and second conversion functions unique to the first and the second tissue types, wherein the first conversion function is based on the first proton projection value, and the second conversion function is based on the second proton projection value modified by the first conversion function; and
   (e) producing a treatment control sequence defining proton energies along different paths through the patient tissue using the derived proton stopping power data according to a predefined treatment plan.

2. The program of claim 1 wherein the photon attenuation data provides attenuation of megavoltage photons.

3. The program of claim 1 wherein the photon attenuation data provides attenuation of kilovoltage photons.

4. The program of claim 1 further including the step of receiving partial proton stopping power data of the patient insufficient to reconstruct a tomographic image and wherein step (e) uses the derived proton stopping power data to complete the partial proton stopping power data to reconstruct a tomographic image revealing proton stopping power, and using the tomographic image revealing proton stopping power to produce the treatment control sequence.

5. The program of claim 1 wherein the derived, proton stopping power data is sufficient to reconstruct a tomographic image and including the step of using the derived proton stopping power data to reconstruct a tomographic image revealing proton stopping power, and using the tomographic image revealing proton stopping power to produce the treatment control sequence.

6. The program of claim 1 wherein step (d) further includes the step of determining the conversion functions by analyzing the attenuation of x-ray photons along different paths through the patient through different tissue types.

7. The program of claim 6 wherein the analysis mathematically combines attenuation of x-ray photons through different combinations of the different tissue types to isolate an attenuation value for each tissue type.

8. The program of claim 6 wherein the analysis further analyzes attenuation of x-ray photons through a phantom material simulating one tissue type in isolation.

9. The program of claim 8 wherein the phantom is a water phantom representing non-adipose tissue.

10. The program of claim 6 wherein the analysis fits a mathematical function to measured data.

11. The program of claim 1 wherein the tissue types are selected from at least two of the group consisting of adipose tissue, non-adipose tissue, and cortical bone tissue.

12. The program of claim 1 wherein step (b) segments at least three tissue types.

13. A method of preparing a treatment control sequence for proton radiotherapy comprising the steps of:
  (a) obtaining photon attenuation image of a patient based on attenuation data of x-ray photons passing through patient tissue;
  (b) segmenting the obtained photon attenuation image into at least two tissue types;
  (c) receiving a first proton projection value for a proton beamlet passing through one of the at least two tissue types of the patient tissue while avoiding another of the at least two tissue types, and receiving a second proton projection value for a proton beamlet passing through at least the other of the at least two tissue types;
  (d) converting at least a portion of the photon attenuation data to derived proton stopping power data using different conversion functions unique to each tissue type, wherein the conversion functions are based on the first and second proton projection values;
  (e) obtaining partial proton stopping power data of the patient insufficient to reconstruct a tomographic image;
  (f) outputting a treatment control sequence defining proton energies along different paths through the patient tissue using the derived proton stopping power data; and
  wherein step (f) uses the derived proton stopping power data to complete the partial proton stopping power data to reconstruct a tomographic image revealing proton stopping power, and using the tomographic image revealing proton stopping power to produce the treatment control sequence.

14. The method of claim 13 wherein the photon attenuation data provides attenuation of megavoltage photons.

15. The method of claim 13 wherein the photon attenuation data provides attenuation of kilovoltage photons.

16. The method of claim 13 wherein the derived proton stopping power data is sufficient to reconstruct a tomographic image and including the step of using the derived proton stopping power data to reconstruct a tomographic image revealing proton stopping power, and using the tomographic image revealing proton stopping power to produce the treatment control sequence.

17. The method of claim 13 wherein the tissue types are selected from at least two of the group consisting of adipose tissue, non-adipose tissue, and cortical bone tissue.

18. The method of claim 13 wherein step (b) segments at least three tissue types.

19. A treatment planning system comprising an electronic computer executing a stored program to:
  (a) receive a photon attenuation image of a patient based on attenuation data of x-ray photons passing through patient tissue;
  (b) segment the received photon attenuation image into at least first and second tissue types of the patient tissue;
  (c) receive a first proton projection value for a proton beamlet passing through the first tissue type while avoiding the second tissue type;
  (d) receive a second proton projection value for a proton beamlet passing through the second tissue type while avoiding the first tissue type;
  (e) convert at least a portion of the photon attenuation data to derived proton stopping power data using first and second conversion functions unique to the first and second tissue types, respectively, wherein the first and second conversion functions are based on the first and second proton projection values, respectively, and wherein the first and second conversion functions are averaged based on the amounts of the first and second tissue types; and
  (f) produce a treatment control sequence defining proton energies along different paths through the patient tissue using the derived proton stopping power data.

* * * * *